(12) United States Patent
Clasby et al.

(10) Patent No.: US 7,713,985 B2
(45) Date of Patent: May 11, 2010

(54) ADENOSINE $A_{a2}$ RECEPTOR ANTAGONISTS

(75) Inventors: Martin C. Clasby, Plainsboro, NJ (US); Samuel Chackalamannil, Califon, NJ (US); Andrew Stamford, Chatham Township, NJ (US)

(73) Assignee: Schering Corporation, Kenilworth, NJ (US)

( * ) Notice: Subject to any disclaimer, the term of this patent is extended or adjusted under 35 U.S.C. 154(b) by 365 days.

(21) Appl. No.: 11/767,624

(22) Filed: Jun. 25, 2007

(65) Prior Publication Data

US 2008/0255156 A1  Oct. 16, 2008

Related U.S. Application Data

(60) Provisional application No. 60/816,516, filed on Jun. 26, 2006.

(51) Int. Cl.
   *A01N 43/54*   (2006.01)
   *A61K 31/505*  (2006.01)
   *C07D 491/00*  (2006.01)

(52) U.S. Cl. .................... 514/267; 544/251

(58) Field of Classification Search ........... 514/267; 544/251
   See application file for complete search history.

(56) References Cited

FOREIGN PATENT DOCUMENTS

| WO | WO 99/18106    | 4/1999  |
|----|----------------|---------|
| WO | WO 2004/058974 | 7/2004  |
| WO | WO 2006/138734 | 12/2006 |
| WO | WO 2007/035542 | 3/2007  |

OTHER PUBLICATIONS

Baraldi, et al., Recent Developments in the Field of A2A and A3 Adenosine Receptor Antagonists, Eur. J. of Med. Chem., 38, 367-382 (2003).*

Baraldi., et al., "Recent developments in the field of $A_{2A}$ and $A_3$ adenosine receptor antagonists", European Journal of Medicinal Chemistry, vol. 38, No. 4, pp. 367-382, (2003).

Holschbach, et al., "Derivatives of 4,6-diamino-1,2-dihydro-2-phenyl-1,2,4-tri azolo[4,3-a] quinoxalin-2*H*-1-one: potential antagonist ligands for imaging the $A_{2A}$ adenosine receptor by positron emission tomography (PET)", European Journal of Medicinal Chemistry, vol. 40, No. 5, pp. 421-437, (2005).

PCT Internal Search Report mail date May 16, 2008 for corresponding PCT Application No. PCT/US2007/014886.

* cited by examiner

*Primary Examiner*—James O Wilson
*Assistant Examiner*—Erich A Leeser
(74) *Attorney, Agent, or Firm*—Krishna G. Banerjee; William Y. Lee

(57) ABSTRACT

Compounds having the structural formula I

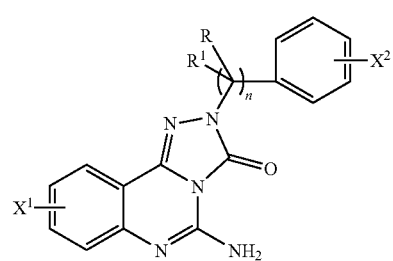

or a pharmaceutically acceptable salt thereof, wherein:
   $X^1$ and $X^2$ are 1-3 substituents independently selected from the group consisting of H, alkyl, halo, —$CF_3$, —$OCF_3$, alkoxy, —OH and —CN;
   n is 0, 1 or 2; and
   R and $R^1$ are H or alkyl;
also disclosed is the use of the compounds in the treatment of CNS diseases such as Parkinson's disease, alone or in combination with other agents for treating CNS diseases, pharmaceutical compositions comprising them and kits comprising the components of the combinations.

13 Claims, No Drawings

ADENOSINE A$_{a2}$ RECEPTOR ANTAGONISTS

This application claims the benefit of priority of U.S. Ser. No. 60/816,516, filed on Jun. 26, 2006.

BACKGROUND

The present invention relates to adenosine A$_{2a}$ receptor antagonists, the use of said compounds in the treatment of central nervous system diseases, in particular Parkinson's disease, and to pharmaceutical compositions comprising said compounds.

Adenosine is known to be an endogenous modulator of a number of physiological functions. At the cardiovascular system level, adenosine is a strong vasodilator and a cardiac depressor. On the central nervous system, adenosine induces sedative, anxiolytic and antiepileptic effects. On the respiratory system, adenosine induces bronchoconstriction. At the kidney level, it exerts a biphasic action, inducing vasoconstriction at low concentrations and vasodilation at high doses. Adenosine acts as a lipolysis inhibitor on fat cells and as an antiaggregant on platelets.

Adenosine action is mediated by the interaction with different membrane specific receptors which belong to the family of receptors coupled with G proteins. Biochemical and pharmacological studies, together with advances in molecular biology, have allowed the identification of at least four subtypes of adenosine receptors: A$_1$, A$_{2a}$, A$_{2b}$ and A$_3$. A$_1$ and A$_3$ are high-affinity, inhibiting the activity of the enzyme adenylate cyclase, and A$_{2a}$ and A$_{2b}$ are low-affinity, stimulating the activity of the same enzyme. Analogs of adenosine able to interact as antagonists with the A$_1$, A$_{2a}$, A$_{2b}$ and A$_3$ receptors have also been identified.

Selective antagonists for the A$_{2a}$ receptor are of pharmacological interest because of their reduced level of side affects. In the central nervous system, A$_{2a}$ antagonists can have antidepressant properties and stimulate cognitive functions. Moreover, data has shown that A$_{2a}$ receptors are present in high density in the basal ganglia, known to be important in the control of movement. Hence, A$_{2a}$ antagonists can improve motor impairment due to neurodegenerative diseases such as Parkinson's disease, senile dementia as in Alzheimer's disease, and psychoses of organic origin.

Some xanthine-related compounds have been found to be A$_1$ receptor selective antagonists, and xanthine and non-xanthine compounds have been found to have high A$_{2a}$ affinity with varying degrees of A$_{2a}$ vs. A$_1$ selectivity. Certain imidazolo- and pyrazolo-substituted triazolo-pyrimidine adenosine A$_{2a}$ receptor antagonists have been disclosed previously, for example in WO 95/01356; WO 97/05138; and WO 98/52568. Certain pyrazolo-substituted triazolo-pyrimidine adenosine A$_{2a}$ receptor antagonists are disclosed in U.S. Ser. No. 09/207,143, filed May 24, 2001. Certain imidazolo-substituted triazolo-pyrimidine adenosine A$_{2a}$ receptor antagonists are disclosed in U.S. Provisional Application 60/329,567, filed Oct. 15, 2001. U.S. Pat. No. 5,565,460 discloses certain triazolo-triazines as antidepressants; EP 0976753 and WO 99/43678 disclose certain triazolo-pyrimidines as adenosine A$_{2a}$ receptor antagonists; and WO 01/17999 discloses certain triazolo pyridines as adenosine A$_{2a}$ receptor antagonists.

SUMMARY OF THE INVENTION

The present invention relates to a compound represented by the structural formula I

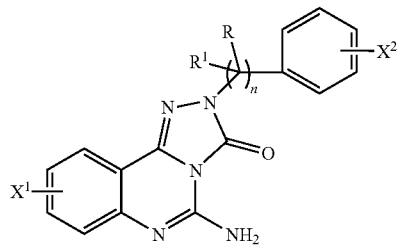

or a pharmaceutically acceptable salt, solvate, prodrug or enantiomer thereof, wherein:

X$^1$ is 1-3 substituents independently selected from the group consisting of H, alkyl, halo, —CF$_3$, —OCF$_3$, alkoxy, —OH and —CN;

X$^2$ is 1-3 substituents independently selected from the group consisting of H, alkyl, halo, —CF$_3$, —OCF$_3$, alkoxy, —OH and —CN;

n is 0, 1 or 2; and

R and R$^1$ are independently selected from the group consisting of H and alkyl.

Another aspect of the invention is a pharmaceutical composition comprising a therapeutically effective amount of at least one compound of formula I in a pharmaceutically acceptable carrier.

Yet another aspect of the invention is a method of treating central nervous system diseases such as depression, cognitive diseases and neurodegenerative diseases such as Parkinson's disease, Alzheimer's disease, senile dementia or psychoses, and stroke, comprising administering at least one compound of formula I to a mammal in need of such treatment.

The invention also relates to the treatment of attention related disorders such as attention deficit disorder (ADD) and attention deficit hyperactivity disorder (ADHD). The invention also relates to the treatment or prevention of Extra-Pyramidal Syndrome (e.g., dystonia, akathisia, pseudoparkinsonism and tardive dyskinesia), the treatment of primary (idiopathic) dystonia, and the treatment or prevention of dystonia in patients who exhibit dystonia as a result of treatment with a tricyclic antidepressant, lithium or an anticonvulsant, or who have used cocaine, comprising administering at least one compound of formula I to a mammal in need of such treatment. The invention further relates to treatment of abnormal movement disorders such as restless leg syndrome (RLS) or periodic limb movement in sleep (PLMS), comprising administering to a patient in need thereof a therapeutically effective amount of at least one compound of formula I.

In particular, the invention is drawn to the method of treating Parkinson's disease comprising administering at least one compound of formula I to a mammal in need of such treatment.

Still another aspect of the invention is a method of treating Parkinson's disease with a combination of at least one compound of formula I and one or more agents useful in the treatment of Parkinson's disease, for example dopamine; a dopaminergic agonist; an inhibitor of monoamine oxidase, type B (MAO-B); a DOPA decarboxylase inhibitor (DCI); a catechol-O-methyltransferase (COMT) inhibitor; or a (N-methyl-D-aspartic acid) (NMDA) receptor antagonist. Also claimed is a pharmaceutical composition comprising at least one compound of formula I and one or more agents known to be useful in the treatment of Parkinson's in a pharmaceutically acceptable carrier.

The invention also comprises a method of treating EPS, dystonia, RLS or PLMS comprising administering a combination of at least one compound of formula I with another agent useful in treating RLS or PLMS, such as levodopa/carbidopa, levodopa/benserazide, a dopamine agonist, a benzodiazepine, an opioid, an anticonvulsant or iron, to a patient in need thereof.

In the method comprising the administration of the combination of the invention, one or more compounds of formula I and one or more other anti-Parkinson's agents can be administered simultaneously or sequentially in separate dosage forms. Similarly, one or more compounds of formula I and one or more other agents useful in treating EPS, dystonia, RLS or PLMS can be administered simultaneously or sequentially in separate dosage forms. Therefore, also claimed is a kit comprising in separate containers in a single package pharmaceutical compositions for use in combination to treat Parkinson's disease wherein one container comprises a pharmaceutical composition comprising an effective amount of a compound of formula I in a pharmaceutically acceptable carrier, and wherein, in separate containers, one or more pharmaceutical compositions each comprise an effective amount of an agent useful in the treatment of Parkinson's disease, EPS, dystonia, RLS or PLMS in a pharmaceutically acceptable carrier.

DETAILED DESCRIPTION

Referring to compounds of formula I above, preferred compounds of formula I are those wherein n is 1. Also preferred are compounds of formula I wherein R and $R^1$ are each H.

$X^1$ is preferably 1 or 2 substituents independently selected from H, halo, alkyl, alkoxy and —$CF_3$; more preferably, $X^1$ is 1 or 2 substituents independently selected from H, fluoro, chloro, methyl, methoxy and —$CF_3$.

$X^2$ is preferably 1, 2 or 3 substituents independently selected from H, halo, alkyl, alkoxy, —$CF_3$, —$OCF_3$ and —CN; more preferably, $X^2$ is 1, 2 or 3 substituents independently selected from H, fluoro, chloro, methyl, methoxy, —$CF_3$, —$OCF_3$ and —CN.

Preferred compounds are those of Examples 2, 8, 12, 13 and 31, shown below.

As used herein, the term "alkyl" means an aliphatic hydrocarbon group which may be straight or branched and comprising about 1 to about 6 carbon atoms in the chain. Branched means that one or more lower alkyl groups such as methyl, ethyl or propyl, are attached to a linear alkyl chain. Non-limiting examples of suitable alkyl groups include methyl, ethyl, n-propyl, isopropyl, n-butyl, t-butyl and n-pentyl.

Alkoxy means an alkyl-O-group in which the alkyl group is as previously described. Non-limiting examples of suitable alkoxy groups include methoxy, ethoxy n-propoxy, isopropoxy and n-butoxy. The bond to the parent moiety is through the ether oxygen.

Halo means fluoro, chloro, bromo or iodo.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound' or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

The term "purified", "in purified form" or "in isolated and purified form" for a compound refers to the physical state of said compound after being isolated from a synthetic process (e.g. from a reaction mixture), or natural source or combination thereof. Thus, the term "purified", "in purified form" or "in isolated and purified form" for a compound refers to the physical state of said compound after being obtained from a purification process or processes described herein or well known to the skilled artisan (e.g., chromatography, recrystallization and the like), in sufficient purity to be characterizable by standard analytical techniques described herein or well known to the skilled artisan.

It should also be noted that any carbon as well as heteroatom with unsatisfied valences in the text, schemes, examples and Tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

When any variable (e.g., $X^2$, etc.) occurs more than one time in any constituent or in Formula I, its definition on each occurrence is independent of its definition at every other occurrence.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g., a drug precursor) that is transformed in vivo to yield a compound of Formula (I) or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if a compound of Formula (I) or a pharmaceutically acceptable salt, hydrate or solvate of the compound contains a carboxylic acid functional group, a prodrug can comprise an ester formed by the replacement of the hydrogen atom of the acid group with a group such as, for example, $(C_1-C_8)$alkyl, $(C_2-C_{12})$alkanoyl-oxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxy-carbonyl)amino) ethyl having from 4 to 10 carbon atoms, 3-phthalidyl, 4-crotono-lactonyl, gamma-butyrolacton-4-yl, di-N,N—($C_1$-$C_2$) alkylamino($C_2$-$C_3$)alkyl (such as β-dimethylaminoethyl), carbamoyl-($C_1$-$C_2$)alkyl, N,N-di($C_1$-$C_2$)alkylcarbamoyl-(C1-C2)alkyl and piperidino-, pyrrolidino- or morpholino ($C_2$-$C_3$)alkyl, and the like.

Similarly, if a compound of Formula (I) contains an alcohol functional group, a prodrug can be formed by the replacement of the hydrogen atom of the alcohol group with a group such as, for example, ($C_1$-$C_6$)alkanoyloxymethyl, 1-(($C_1$-$C_6$)alkanoyloxy)-ethyl, 1-methyl-1-(($C_1$-$C_6$)alkanoyloxy)ethyl, ($C_1$-$C_6$)alkoxycarbonyloxymethyl, N—($C_{1-6}$)alkoxycarbonylaminomethyl, succinoyl, ($C_1$-$C_6$)alkanoyl, α-amino($C_1$-$C_4$)alkanyl, arylacyl and α-aminoacyl, or α-aminoacyl-α-aminoacyl, where each α-aminoacyl group is independently selected from the naturally occurring L-amino acids, P(O)(OH)$_2$, —P(O)(O($C_1$-$C_6$)alkyl)$_2$ or glycosyl (the radical resulting from the removal of a hydroxyl group of the hemiacetal form of a carbohydrate), and the like.

If a compound of Formula (I) incorporates an amine functional group, a prodrug can be formed by the replacement of a hydrogen atom in the amine group with a group such as, for example, R-carbonyl, RO-carbonyl, NRR'-carbonyl where R and R' are each independently ($C_1$-$C_{10}$)alkyl, ($C_3$-$C_7$) cycloalkyl, benzyl, or R-carbonyl is a natural α-aminoacyl or natural β-aminoacyl, —C(OH)C(O)OY$^1$ wherein Y$^1$ is H, ($C_1$-$C_6$)alkyl or benzyl, —C(OY$^2$)Y$^3$ wherein Y$^2$ is ($C_1$-$C_4$) alkyl and Y$^3$ is ($C_1$-$C_6$)alkyl, carboxy($C_1$-$C_6$)alkyl, amino ($C_1$-$C_4$)alkyl or mono-N— or di-N,N—($C_1$-$C_6$)alkylaminoalkyl, —C(Y$^4$)Y$^5$ wherein Y$^4$ is H or methyl and Y$^5$ is mono-N— or di-N,N—($C_1$-$C_6$)alkylamino morpholino, piperidin-1-yl or pyrrolidin-1-yl, and the like.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is H$_2$O.

One or more compounds of the invention may optionally be converted to a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTech.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

"Effective amount" or "therapeutically effective amount" is meant to describe an amount of compound or a composition of the present invention effective in inhibiting the above-noted diseases and thus producing the desired therapeutic, ameliorative, inhibitory or preventative effect.

The compounds of Formula I can form salts which are also within the scope of this invention. Reference to a compound of Formula I herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula I contains both a basic moiety and an acidic moiety, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula I may be formed, for example, by reacting a compound of Formula I with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Pharmaceutically acceptable esters of the present compounds include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2)

sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di($C_{6-24}$)acyl glycerol.

The compounds of Formula (I) may contain asymmetric or chiral centers, and, therefore, exist in different stereoisomeric forms. It is intended that all stereoisomeric forms of the compounds of Formula (I) as well as mixtures thereof, including racemic mixtures, form part of the present invention. In addition, the present invention embraces all geometric and positional isomers. For example, if a compound of Formula (I) incorporates a double bond or a fused ring, both the cis- and trans-forms, as well as mixtures, are embraced within the scope of the invention.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of Formula (I) may be atropisomers (e.g., substituted biaryls) and are considered as part of this invention. Enantiomers can also be separated by use of chiral HPLC column.

It is also possible that the compounds of Formula (I) may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). (For example, if a compound of Formula (I) incorporates a double bond or a fused ring, both the cis- and trans-forms, as well as mixtures, are embraced within the scope of the invention).

Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

The present invention also embraces isotopically-labelled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

Certain isotopically-labelled compounds of Formula (I) (e.g., those labeled with $^3H$ and $^{14}C$) are useful in compound and/or substrate tissue distribution assays. Tritiated (i.e., $^3H$) and carbon-14 (i.e., $^{14}C$) isotopes are particularly preferred for their ease of preparation and detectability. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Isotopically labelled compounds of Formula (I) can generally be prepared by following procedures analogous to those disclosed in the Schemes and/or in the Examples hereinbelow, by substituting an appropriate isotopically labelled reagent for a non-isotopically labelled reagent.

Polymorphic forms of the compounds of Formula I, and of the salts, solvates, esters and prodrugs of the compounds of Formula I, are intended to be included in the present invention.

"Patient" includes both human and animals.

"Mammal" means humans and other mammalian animals.

Lines drawn into the ring systems, such as, for example:

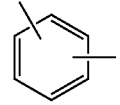

indicate that the indicated line (bond) may be attached to any of the substitutable ring carbon atoms.

As well known in the art, a bond drawn from a particular atom wherein no moiety is depicted at the terminal end of the bond indicates a methyl group bound through that bond to the atom, unless stated otherwise. For example:

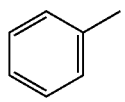

represents

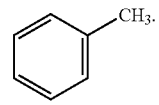

Compounds of formula I are prepared by general methods known in the art. Preferably, the compounds of formula I are prepared by the methods shown in the following reaction schemes. In the Schemes and examples that follow, the following abbreviations are used:

| | |
|---|---|
| AcOH | acetic acid |
| Boc | (tert-butoxycarbonyl) |
| DMSO | ($d_6$-dimethylsulfoxide) |
| DIPEA | (diisopropylethylamine) |

-continued

| | |
|---|---|
| Dioxane | (1,4-dioxane) |
| EtOAc | (ethyl acetate) |
| EtOH | (ethanol) |
| Ether | (diethyl ether) |
| KOCN | (potassium cyanate) |
| LCMS | (liquid chromatography mass spectrometry) |
| MeCN | (acetonitrile) |
| MeOH | (methanol) |
| Room temperature, rt. | (about 25° C.) |
| $SiO_2$ | (silica gel for flash chromatography) |
| TEA | (triethylamine) |
| TLC | (thin layer chromatography) |
| THF | (tetrahydrofuran) |

Where NMR data are presented, $^1$H spectra were obtained on either a Varian Gemini-400BB, or Mercury-400BB and are reported as ppm (parts per million) downfield from $Me_4Si$ with number of protons, multiplicities (s=singlet, d=doublet, t=triplet, m=multiplet, br.=broad), and coupling constants in hertz. Where LCMS data are presented, analyses were performed using an applied biosystems API-100 mass spectrometer and Shimadzu SCL-10A LC column: Altech platinum C18, 3 micron, 33 mm×7 mm ID: gradient flow: 0 min-10% MeCN, 5 min-95% MeCN, 7 min-95% MeCN, 7.5 min-10% MeCN, 9 min-stop. The observed parent ion is given.

In general, compounds of this invention can be synthesized by combining dichlorides of type 1 and hydrazines of type 2. The intermediates of type 3 are then treated with phosgene to form the cyclic compounds of type 4, which are then converted to the target examples 5 by treatment with ammonia under microwave conditions (Scheme 1).

Scheme 1

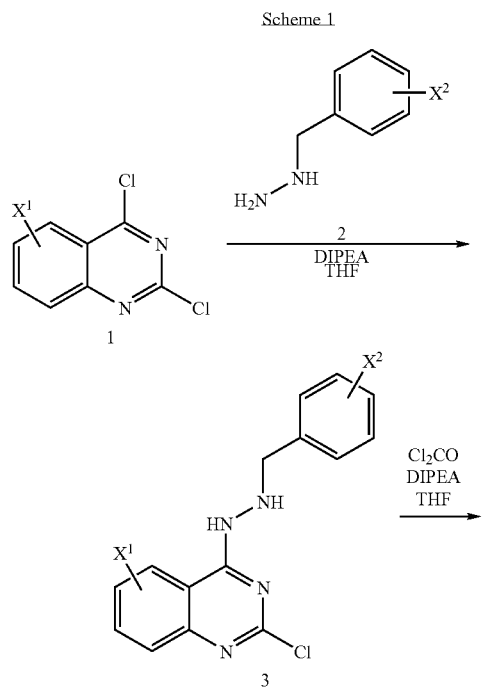

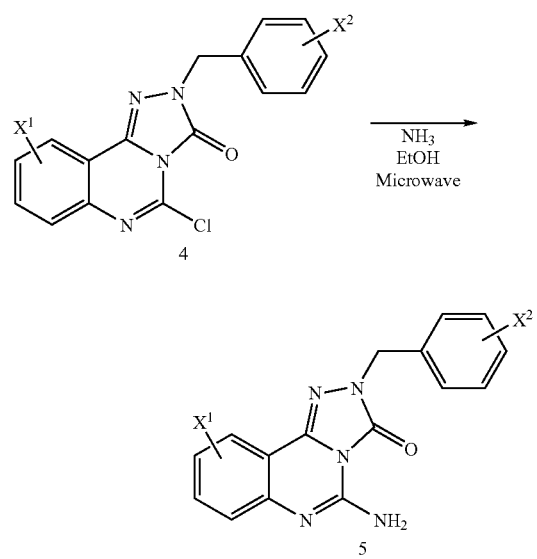

Compounds of types 6 and 7 are made similarly from phenyl hydrazine 8 and phenethyl hydrazine 9 respectively (Scheme 2).

Scheme 2

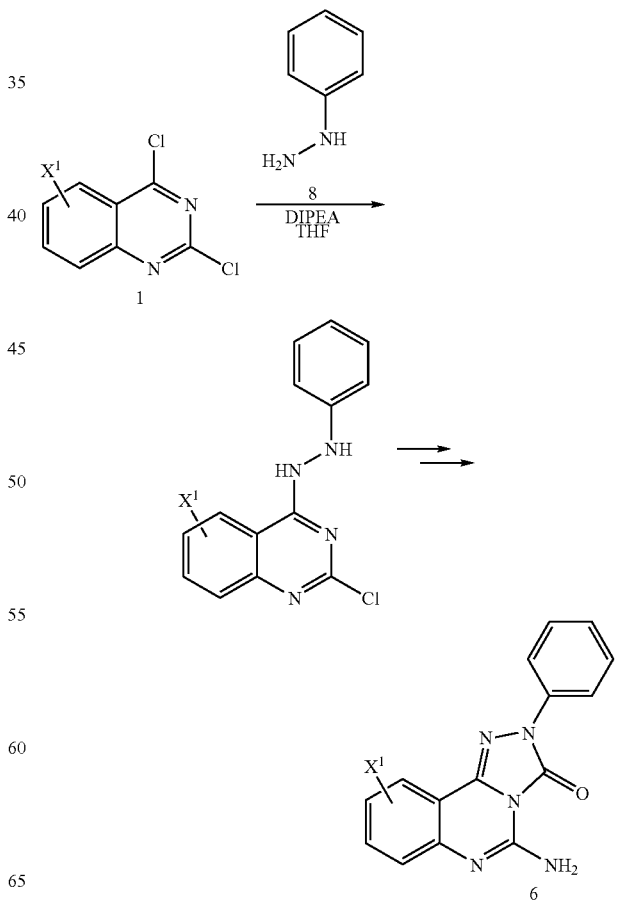

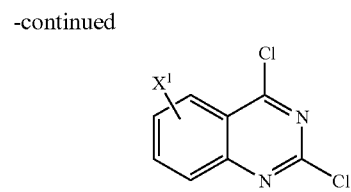

The hydrazines 2 are readily available from benzyl bromides of type 12 or benzyl chlorides of type 13 in two steps via displacement of the halide with tert-butyl carbazate and removal of the Boc protecting group with HCl (Scheme 4).

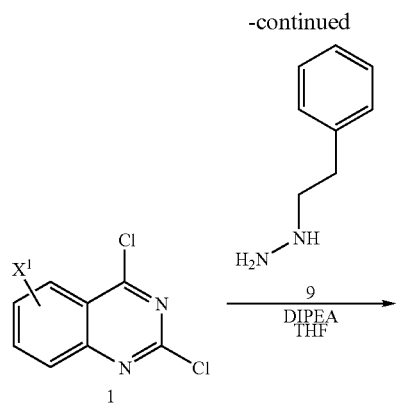

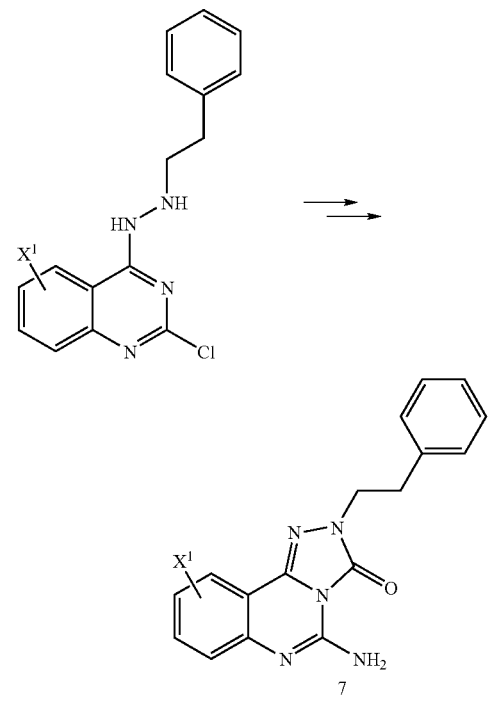

The dichlorides 1 are available from anthranilic acids of type 10 in two steps via condensation with KOCN or urea followed by treatment with POCl₃ (Scheme 3).

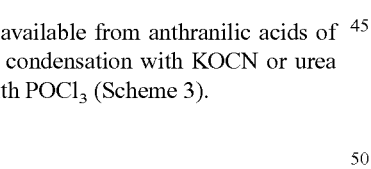

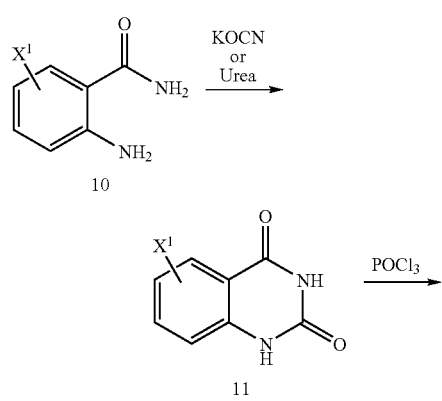

PREPARATIVE EXAMPLES

Prep. 1

4-Fluorobenzyl chloride (0.9 ml, 0.0076 mol) was added to tert-butyl carbazate (4 g, 4 eq) in EtOH (10 ml). DIPEA (1.25 ml, 1 eq) was added and the mixture heated at 60° C. for 3 h. After cooling to rt, the mixture was diluted with EtOAc, washed with $NH_4Cl_{(sat)}$, $NaHCO_{3(sat)}$, dried ($MgSO_4$), and concentrated to give an oil. Purification by column chromatography (0-20% EtOAc in hexane) gave 650 mg of a residue that was dissolved in 1,4-dioxane/water (7 ml/0.7 ml) and treated with 4M HCl in dioxane (7 ml). After 5 h, ether was added and the resulting precipitate collected to give 451 mg of the title compound. $^1$H NMR (DMSO) δ 3.97 (s, 2H), 7.16 (t, J=8.8 Hz, 2H), 7.37-7.41 (m, 2H).

Using procedures similar to those for preparative example 1, the following preparative examples were synthesized from the appropriate starting materials.

| Preparative Example | Structure | Data |
| --- | --- | --- |
| P2 | 4-Cl-C6H4-CH2-NH-NH2 | $^1$H NMR (DMSO) δ 3.96 (s, 2H), 7.35-7.70 (m, 4H). |
| P3 | 2-CF3-C6H4-CH2-NH-NH2 | $^1$H NMR (DMSO) δ 4.13 (s, 2H), 7.45-7.50 (m, 1H), 7.63-7.69 (m, 3H). |
| P4 | 3-MeO-C6H4-CH2-NH-NH2 | $^1$H NMR (DMSO) δ 3.69 (s, 3H), 3.96 (s, 2H), 6.83-6.86 (m, 1H), 6.90 (d, J = 7.2 Hz, 1H), 6.96 (s, 1H), 7.23 (t, J=8 Hz, 1H). |
| P5 | 2-F-C6H4-CH2-NH-NH2 | $^1$H NMR (DMSO) δ 4.01 (s, 2H), 7.17 (t, J = 8 Hz, 2H), 7.32-7.44 (m, 2H). |
| P6 | 3,4-diCl-C6H3-CH2-NH-NH2 | $^1$H NMR (DMSO) δ 3.98 (s, m), 7.32-7.35 (m, 1H), 7.58 (d, J = 8 Hz, 1H), 7.62 (m, 1H). |
| P7 | 2,4-diCl-C6H3-CH2-NH-NH2 | $^1$H NMR (DMSO) δ 4.04 (s, 2H), 7.42 (dd, J = 8.8, 2 Hz, 1H), 7.48 (d, J = 8.8 Hz, 1H), 7.59 (d, J = 2 Hz, 1H). |
| P8 | 3,5-diCl-C6H3-CH2-NH-NH2 | $^1$H NMR (DMSO) δ 3.98 (s, 2H), 7.41 (m, 2H), 7.53 (m, 1H). |

Prep 9

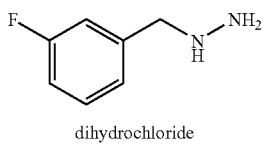

dihydrochloride

3-Fluorobenzyl bromide (0.93 ml, 0.0076 mol) was added to tert-butyl carbazate (4 g, 4 eq) in EtOH (10 ml). The mixture heated at 60° C. for 40 min. After cooling to rt, the mixture was diluted with EtOAc, washed with $NH_4Cl_{(sat)}$, $NaHCO_{3(sat)}$, dried ($MgSO_4$), and concentrated to give an oil. Purification by column chromatography (0-20% EtOAc in hexane) gave 1.07 g of a residue that was dissolved in 1,4-dioxane/water (13.6 ml/1.4 ml) and treated with 4M HCl in dioxane (13.6 ml). After 5 h, the mixture was concentrated to a residue, EtOAc was added and the resulting solid collected by filtration to give 600 mg of the title compound. $^1$H NMR (DMSO) δ 4.0 (s, 2H), 7.08-7.13 (m, 1H), 7.19 (t, J=12.4 Hz, 2H), 7.33-7.38 (m, 1H).

Using procedures similar to those outlined above for preparative example 9, the following preparative examples were synthesized from the appropriate starting materials.

| Preparative Example | Structure | Data |
|---|---|---|
| P10 | 2-Cl-benzyl hydrazine | $^1$H NMR (DMSO) δ 4.08 (s, 2H), 7.26-7.32 (m, 2H), 7.38-7.43 (m, 1H), 7.45-7.49 (m, 1H). |
| P11 | 3-methyl-benzyl hydrazine | $^1$H NMR (DMSO) δ 2.29 (s, 3H), 3.99 (s, 2H), 7.11-7.27 (m, 4H). |
| P12 | 3-CF$_3$-benzyl hydrazine | $^1$H NMR (DMSO) δ 4.07 (s, 2H), 7.54-7.58 (m, 1H), 7.65 (d, J = 7.2 Hz, 2H), 7.71 (br. s, 1H). |
| P13 | 2,3-diCl-benzyl hydrazine | $^1$H NMR (DMSO) δ 4.10 (s, 2H), 7.34 (t, J = 8 Hz, 1H), 7.43 (d, J = 8 Hz, 1H), 7.56 (d, J = 8 Hz, 1H). |
| P14 | 2,5-diCl-benzyl hydrazine | $^1$H NMR (DMSO) δ 4.05 (s, 2H), 7.37 (dd, J = 8.4, 2.8 Hz, 1H), 7.46 (d, J = 8.4 Hz, 1H), 7.50-7.51 (m, 1H). |
| P15 | 3-F-5-Cl-benzyl hydrazine | $^1$H NMR (DMSO) δ 3.99 (s, 2H), 7.21 (d, J = 11.2 Hz, 1H), 7.29 (s, 1H), 7.32-7.37 (m, 1H). |
| P16 | 3-Cl-benzyl hydrazine | $^1$H NMR (DMSO) δ 3.99 (s, 2H), 7.29-7.37 (m, 3H), 7.43 (s, 1H). |

| Preparative Example | Structure | Data |
|---|---|---|
| P17 | phenyl-CH(CH3)-NH-NH2 | ¹H NMR (DMSO) δ 1.68 (br. s, 3H), 4.55 (br. s, 1H), 7.31 (br. s, 3H), 7.52 (br. s 2H). |
| P18 | 3-(OCF3)-C6H4-CH2-NH-NH2 | ¹H NMR (DMSO) δ 4.08 (s, 2H), 7.31 (s, 1H), 7.38-7.44 (m, 2H), 7.50 (t, J = 7.2 Hz, 1H). |
| P19 | 2-CF3-5-Cl-C6H3-CH2-NH-NH2 | ¹H NMR (DMSO) δ 4.17 (s, 2H), 7.60 (d, J = 8.8 Hz, 1H), 7.74-7.77 (m, 2H). |
| P20 | 3-Cl-2-F-C6H3-CH2-NH-NH2 | ¹H NMR (DMSO) δ 4.04 (s, 2H), 7.25 (t, J = 7.6 Hz, 1H), 7.36-7.46 (m, 1H), 7.52-7.60 (m, 1H). |
| P21 | 2-F-5-Cl-C6H3-CH2-NH-NH2 | ¹H NMR (DMSO) δ 4.04 (s, 2H), 7.27 (t, J = 10 Hz, 1H), 7.41-7.46 (m, 1H), 7.51-7.55 (m, 1H). |
| P22 | 2,6-diF-3-Cl-C6H2-CH2-NH-NH2 | ¹H NMR (DMSO) δ 4.07 (s, 2H), 7.20 (t, J = 8.8 Hz, 1H), 7.62-7.69 (m, 1H). |
| P23 | 3-Cl-4-F-C6H3-CH2-NH-NH2 | ¹H NMR (DMSO) δ 4.01 (s, 2H), 7.37-7.44 (m, 2H), 7.63 (d, J = 6.4 Hz, 1H). |
| P24 | 3,5-diF-C6H3-CH2-NH-NH2 | ¹H NMR (DMSO) δ 4.04 (s, 2H), 7.11-7.21 (m, 3H). |

| Preparative Example | Structure | Data |
| --- | --- | --- |
| P25 | 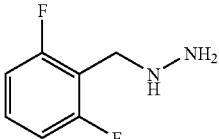 | $^1$H NMR (DMSO) δ 4.00 (s, 2H), 7.08 (t, J = 8 Hz, 2H), 7.42 (q, J = 7.2 Hz). |
| P26 | 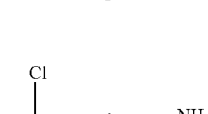 | $^1$H NMR (DMSO) δ 4.20 (s, 2H), 7.32-7.36 (m, 1H), 7.45 (d, J = 8 Hz, 2H), 9.32 (br. m, 3H). |
| P27 | 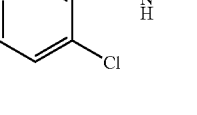 | $^1$H NMR (DMSO) δ 4.07 (s, 2H), 7.57 (d, J = 8 Hz, 2H), 7.68 (d, J = 8 Hz, 2H). |
| P28 | 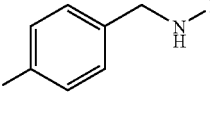 | $^1$H NMR (DMSO) δ 4.03 (s, 2H), 7.53 (t, J = 7.6 Hz, 1H), 7.68 (d, J = 8.4 Hz, 1H), 7.54 (d, J = 8 Hz, 1H), 7.80 (s, 1H). |

Prep. 29

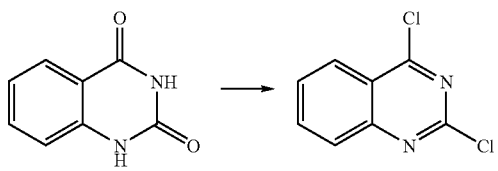

Benzoyleneurea (40 g, 0.25 mol) was dissolved in POCl$_3$ (200 ml), N,N-dimethylaniline (13.2 ml, 0.113 mol) was added and the mixture heated at 130° C. for 5 h. The mixture was then cooled to rt and added to ice; after standing at rt overnight, the mixture was filtered to give a solid which was purified by column chromatography (CH$_2$Cl$_2$) to give the title compound 29, 14 5 g. $^1$H NMR (CDCl$_3$) δ 7.67-7.74 (m, 1H), 7.94-7.98 (m, 2H), 8.22 (d, J=8.8 Hz, 1H).

Prep. 30

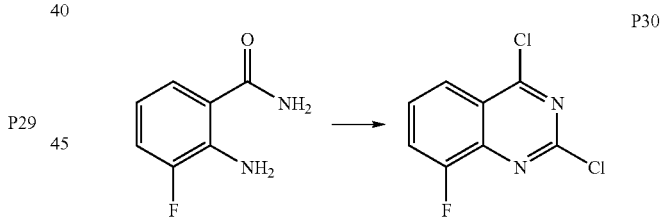

3-Fluoroanthranilic acid (3 g, 0.019 mol) was suspended in water/AcOH (107 ml/1.18 ml). KOCN (2 g, 1.3 eq) in water (11 ml) was added dropwise at 35° C. Once the addition was complete the mixture was heated at 35° C. for 3 h. The mixture was cooled to 0° C. and NaOH (40 g) was added, maintaining the temperature below 40° C. The resulting solid was collected, dissolved in hot water, acidified to pH 3 and 1.5 g (0.0083 mol) of solid was collected by filtration. The solid was dissolved in POCl$_3$ (9 ml), N,N-dimethylaniline (0.65 ml, 0.0051 mol) was added and the mixture heated at 130° C. for 5 h. The mixture was then cooled to rt and added to ice; the resulting solid was collected to give compound 30. $^1$H NMR (DMSO) δ 7.80-7.86 (m, 1H), 8.00 (dd, J=10, 8 Hz, 1H), 8.08 (d, J=8 Hz, 1H).

Using procedures similar to those outlined above for preparative example 30, the following preparative examples were synthesized from the appropriate anthranilic acid.

| Preparative Example | Structure | Data |
|---|---|---|
| P31 | 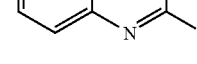 | $^1$H NMR (DMSO) δ 3.93 (s, 3H), 7.42 (d, J = 2.8 Hz, 1H), 7.75 (dd, J = 9.6, 2.8 Hz, 1H), 7.93 (d, J = 9.6 Hz, 1H). |
| P32 | 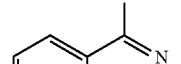 | Ife, R. J. et al. J. Med. Chem. 1995, 38, 2763-2773. |
| P33 | 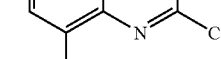 | $^1$H NMR (DMSO) δ 8.01-8.14 (m, 3H). |
| P34 | 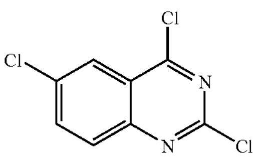 | $^1$H NMR (DMSO) δ 8.04 (d, J = 8.8 Hz, 1H), 8.15 (dd, J = 8.8, 2.4 Hz, 1H), 8.29 (d, J = 2.4 Hz, 1H). |
| P35 | 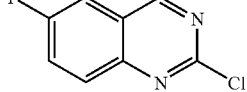 | $^1$H NMR (DMSO) δ 7.75-7.80 (m, 1H), 7.89 (dd, J = 7.6, 2 Hz, 1H), 8.37 (dd, J = 9.6, 6 Hz, 1H). |
| P36 | 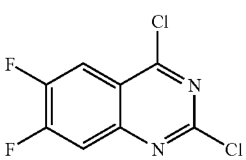 | $^1$H NMR (DMSO) δ 8.18-823 (m, 1H), 8.34-8.39 (m, 1H). |
| P37 | 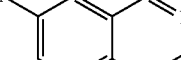 | $^1$H NMR (DMSO) δ 8.18 (dd, J = 12.4, 8 Hz, 1H), 7.84 (d, J = 8 Hz, 1H), 8.06-8.12 (m, 1H). |
| P38 | 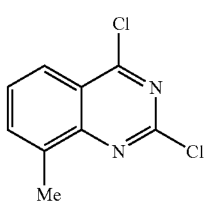 | $^1$H NMR (DMSO) δ 2.60 (s, 3H), 7.73 (t, J = 8 Hz, 1H), 7.97 (d, J = 7.2 Hz, 1H), 8.08 (d, J = 8.4 Hz, 1H). |
| P39 | 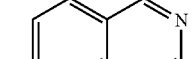 | $^1$H NMR (DMSO) δ 7.46-7.50 (m, 1H), 7.93-7.81 (m, 2H). |

-continued

| Preparative Example | Structure | Data |
|---|---|---|
| P40 | 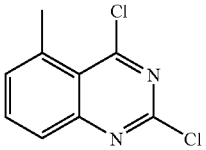 | $^{1}$H NMR (DMSO) δ 2.91 (s, 3H), 7.63 (d, J = 7.2 Hz, 1H), 7.82 (d, J = 8.8 Hz, 1H), 7.93 (t, J = 8 Hz, 1H). |
| P41 | 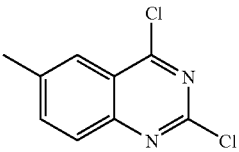 | $^{1}$H NMR (DMSO) δ 2.52 (s, 3H), 7.90 (d, J = 8.8 Hz, 1H), 7.96 (dd, J = 8.8, 2 Hz, 1H), 8.02 (s, 1H). |

Prep. 42

P42

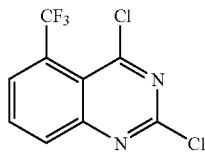

6-Trifluoromethylanthranilic acid (1.485 g, 0.00724 mol) and urea (1.8 g, 4.1 eq) were heated together at 210° C. for 15 min; after cooling to 4, the residue was taken up in hot 2N NaOH, cooled to 0° C. and acidified to pH 3. The resulting solid was suspended in POCl$_3$ (9 ml) and treated with N,N-dimethylaniline (0.38 ml), then heated at 135° C. for 5 h. The mixture was poured onto ice and the solid collected to give 798 mg of 42. $^{1}$H NMR (DMSO) δ 8.19 (t, J=8.4 Hz, 1H), 8.29 (d, J=8.8 Hz, 1H), 8.35 (d, J=7.2 Hz, 1H).

Prep. 43

P43

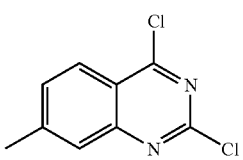

Using procedures similar to those outlined above for preparative example 42, preparative example 43 was synthesized from the appropriate starting materials. $^{1}$H NMR (DMSO) δ 2.54 (s, 3H), 7.70 (dd, J=8.8, 1.6 Hz, 1H), 7.80 (s, 1H), 8.14 (d, J=8.8 Hz, 1H).

Example 1

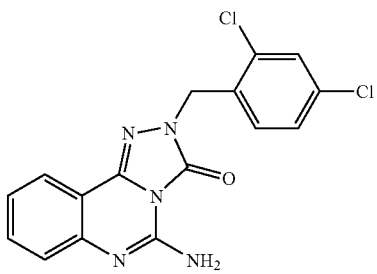

Step 1:

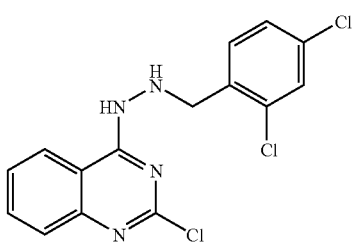

Compound P29 (200 mg, 0.001 mol) and compound P7 (291 mg, 1.1 eq) were dissolved in THF (8 ml), DIPEA (0.88 ml, 5 eq) was added and the mixture was stirred for 2 h. NH$_4$Cl$_{(sat)}$ was added and the mixture extracted with EtOAc; the extracts were dried (MgSO$_4$) and concentrated. The residue was treated with ether and the resulting 300 mg of solid was collected by filtration (MH$^+$=355.2).

Step 2:

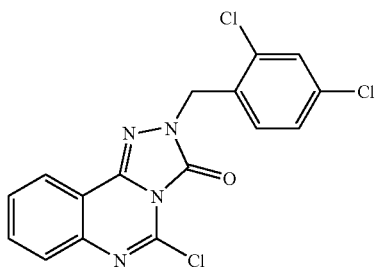

The product of step 1 (300 mg, 0.00085 mol) was dissolved in THF (12 ml), DIPEA (0.227 ml, 1.5 eq) then phosgene (0.68 ml of a 20% solution in toluene) was added. After stirring for 30 min, $NH_4Cl_{(sat)}$ was added and the mixture extracted with $CH_2Cl_2$, dried ($MgSO_4$), and concentrated. The residue was treated with EtOAc and the resulting 288 mg of solid was collected by filtration ($MH^+$=379.2).

Step 3:

The product of step 2 (100 mg, 0.000264 mol) was suspended in EtOH (4 ml) and 2M $NH_3$ in EtOH (0.46 ml, 3.3 eq) was added. The mixture was heated at 80° C. for 20 minutes by microwave. After cooling to rt the solid was collected to give 74 mg of the title compound (Example 1). LCMS $MH^+$=360.2.

Using procedures similar to those outlined above for example 1, the following examples were prepared from the appropriate starting materials.

| Example | Structure | Structural Data |
|---|---|---|
| 2 | 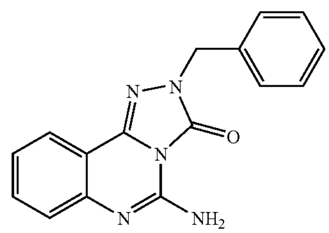 | LCMS $MH^+$ = 292.2 |
| 3 | 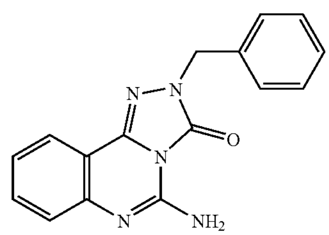 | LCMS $MH^+$ = 278.2 |
| 4 | 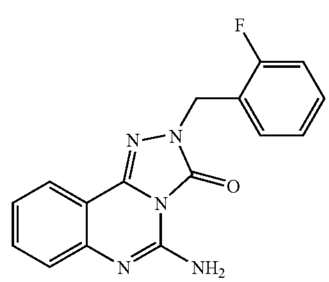 | LCMS $MH^+$ = 310.2 |
| 5 | 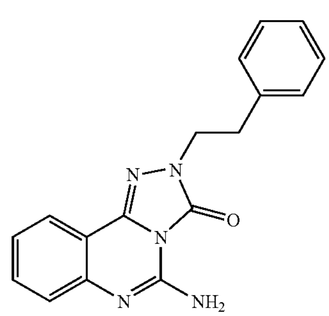 | LCMS $MH^+$ = 306.2 |

-continued
| Example | Structure | Structural Data |
|---------|-----------|-----------------|
| 6 | 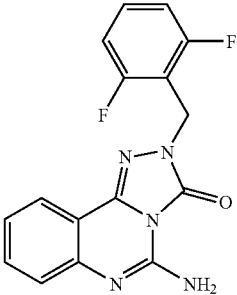 | LCMS MH+ = 328.2 |
| 7 | 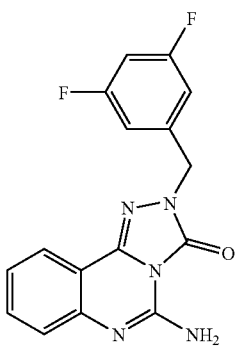 | LCMS MH+ = 328.2 |
| 8 | 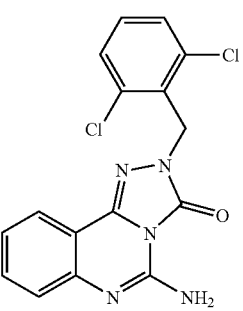 | LCMS MH+ = 362.2 |
| 9 | 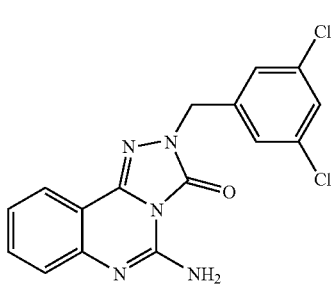 | LCMS MH+ = 360.2 |
| 10 | 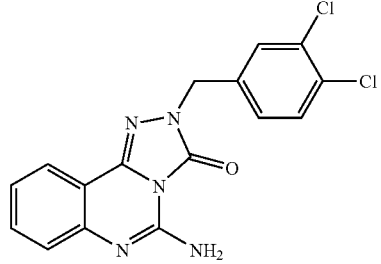 | LCMS MH+ = 360.2 |

-continued

| Example | Structure | Structural Data |
|---|---|---|
| 11 | 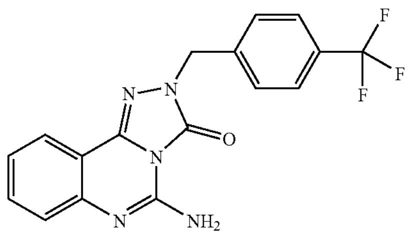 | LCMS MH+ = 360.2 |
| 12 | 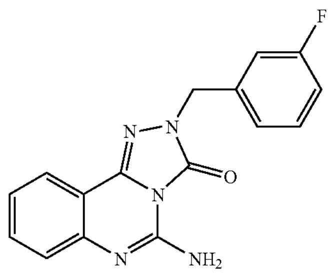 | LCMS MH+ = 310.2 |
| 13 | 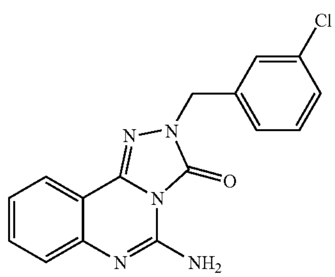 | LCMS MH+ = 326.2 |
| 14 | 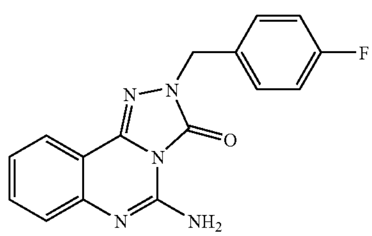 | LCMS MH+ = 310.2 |
| 15 | 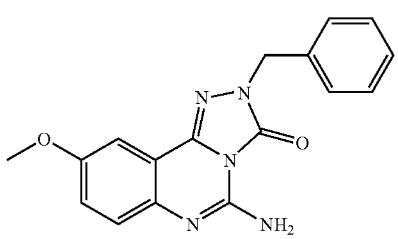 | LCMS MH+ = 322.2 |
| 16 | 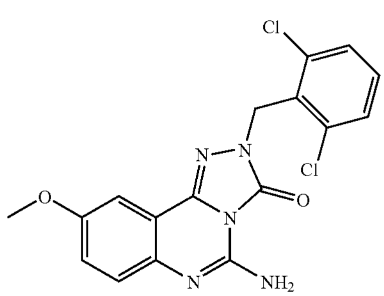 | LCMS MH+ = 390.2 |

-continued

| Example | Structure | Structural Data |
|---|---|---|
| 17 | 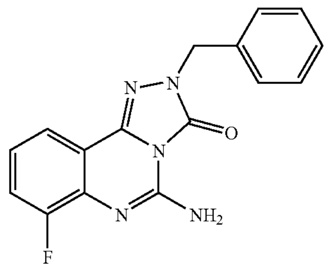 | LCMS MH⁺ = 310.2 |
| 18 | 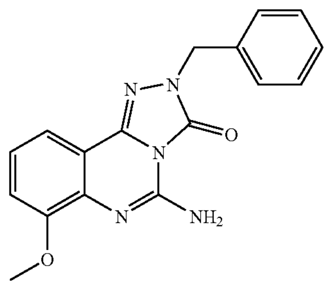 | LCMS MH⁺ = 322.1 |
| 19 | 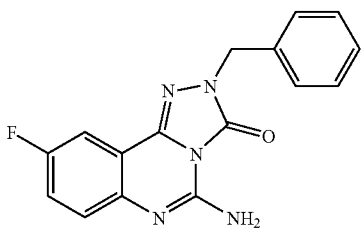 | LCMS MH⁺ = 310.1 |
| 20 | 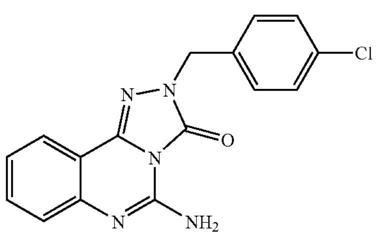 | LCMS MH⁺ = 326.1 |
| 21 | 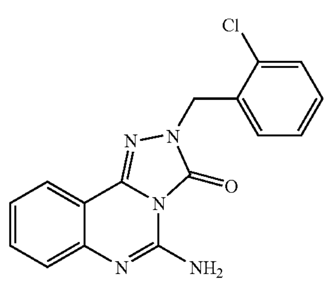 | LCMS MH⁺ = 326.1 |
| 22 | 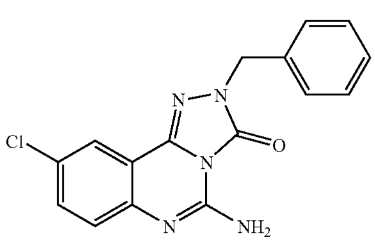 | LCMS MH⁺ = 326.1 |

-continued

| Example | Structure | Structural Data |
|---|---|---|
| 23 | 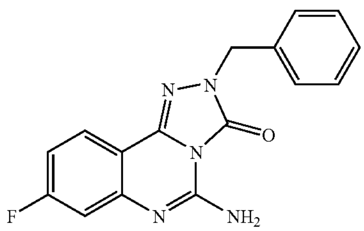 | LCMS MH⁺ = 310.2 |
| 24 | 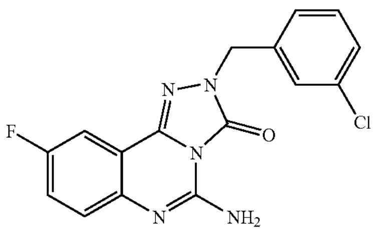 | LCMS MH⁺ = 344.1 |
| 25 | 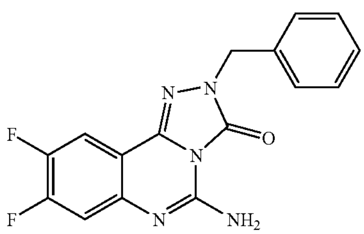 | LCMS MH⁺ = 328.2 |
| 26 | 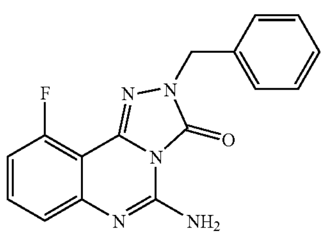 | LCMS MH⁺ = 310.2 |
| 27 | 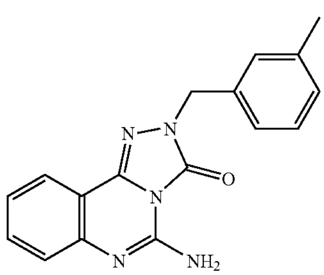 | LCMS MH⁺ = 306.2 |
| 28 | 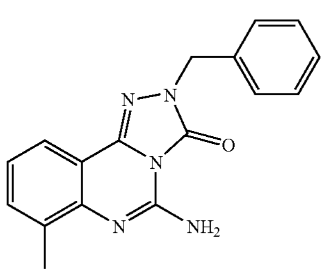 | LCMS MH⁺ = 306.2 |

-continued

| Example | Structure | Structural Data |
|---|---|---|
| 29 | 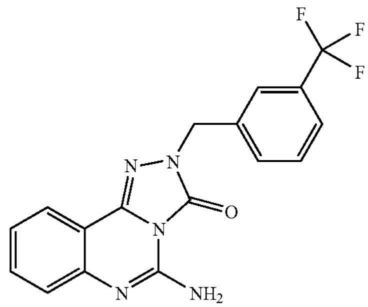 | LCMS MH⁺ = 360.1 |
| 30 | 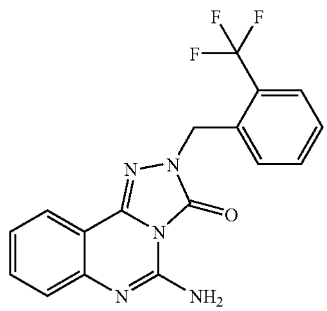 | LCMS MH⁺ = 3601 |
| 31 | 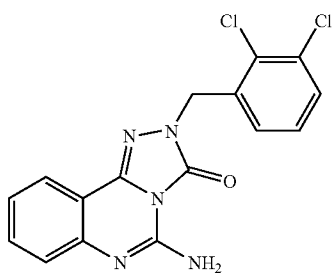 | LCMS MH⁺ = 306.1 |
| 32 | 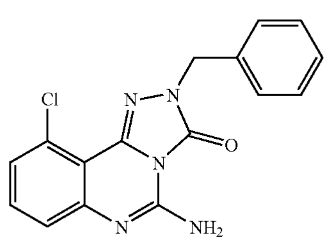 | LCMS MH⁺ = 326.2 |
| 33 | 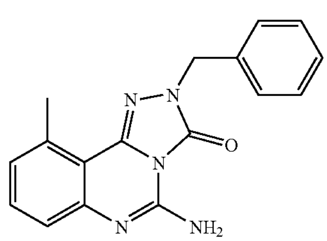 | LCMS MH⁺ = 306.2 |

-continued

| Example | Structure | Structural Data |
|---|---|---|
| 34 | 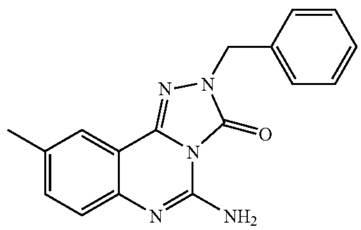 | LCMS MH+ = 306.2 |
| 35 | 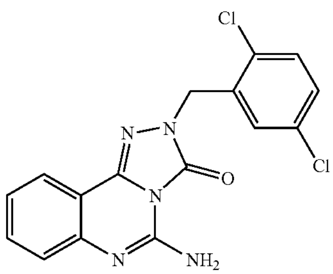 | LCMS MH+ = 360.2 |
| 36 | 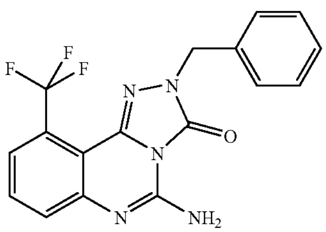 | LCMS MH+ = 360.2 |
| 37 | 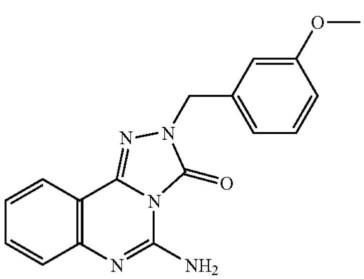 | LCMS MH+ = 322.2 |
| 38 | 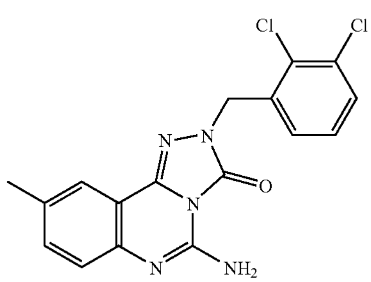 | LCMS MH+ = 374.2 |
| 39 | 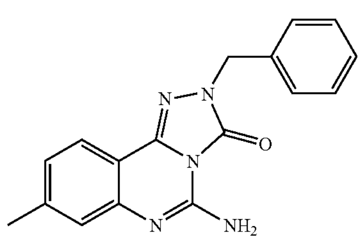 | LCMS MH+ = 306.2 |

-continued

| Example | Structure | Structural Data |
|---------|-----------|-----------------|
| 40 | 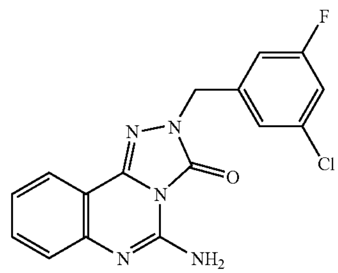 | LCMS MH⁺ = 344.2 |
| 41 | 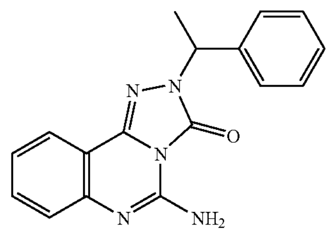 | LCMS MH⁺ = 306.2 |
| 42 | 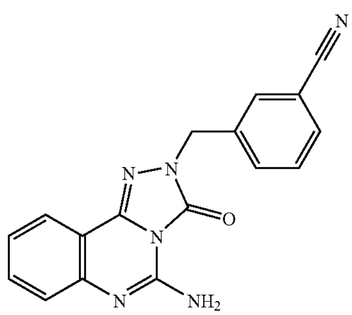 | LCMS MH⁺ = 317.2 |
| 43 | 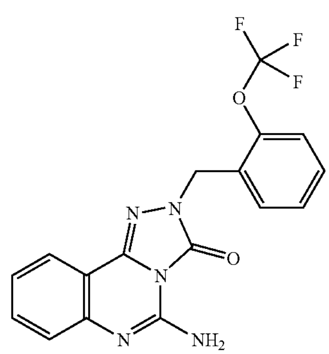 | LCMS MH⁺ = 376.2 |
| 44 | 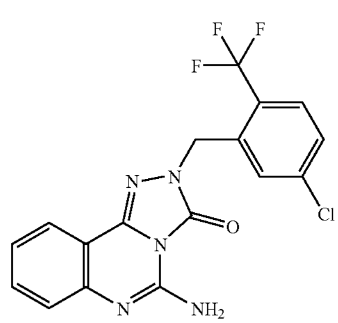 | LCMS MH⁺ = 394.2 |

-continued

| Example | Structure | Structural Data |
|---|---|---|
| 45 | 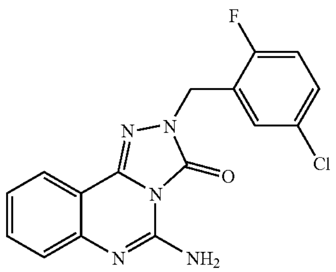 | LCMS MH+ = 344.2 |
| 46 | 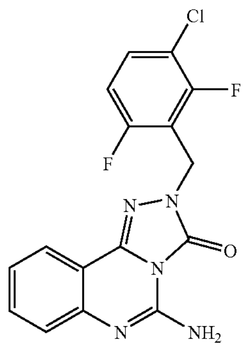 | LCMS MH+ = 362.2 |
| 47 | 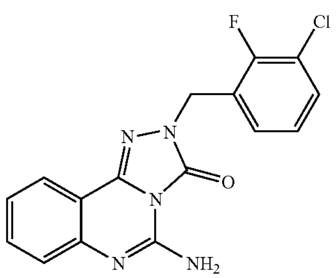 | LCMS MH+ = 344.2 |
| 48 | 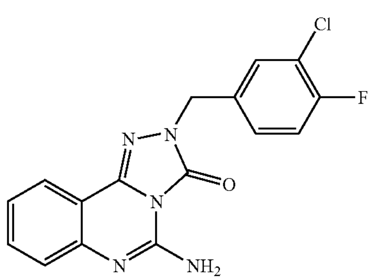 | LCMS MH+ = 344.2 |

Because of their adenosine $A_{2a}$ receptor antagonist activity, compounds of the present invention are useful in the treatment of depression, cognitive function diseases and neurodegenerative diseases such as Parkinson's disease, senile dementia as in Alzheimer's disease, psychoses, attention deficit disorders, EPS, dystonia, RLS and PLMS. In particular, the compounds of the present invention can improve motor-impairment due to neurodegenerative diseases such as Parkinson's disease.

The other agents known to be useful in the treatment of Parkinson's disease that can be administered in combination with the compounds of formula I include: L-DOPA; dopaminergic agonists such as quinpirole, ropinirole, pramipexole, pergolide and bromocriptine; MAO-B inhibitors such as deprenyl and selegiline; DOPA decarboxylase inhibitors such as carbidopa and benserazide; COMT inhibitors such as tolcapone and entacapone; and NMDA receptor antagonists such as amantadine. Amantadine is used as an adjunct to L-DOPA treatment for control of L-DOPA induced dyskinesia.

Adenosine $A_{2a}$ antagonists of the invention can also be co-administered with the antipsychotic agents known to cause the EPS and tricyclic antidepressants known to cause dystonia.

Antipsychotic agents causing the EPS treated by adenosine $A_{2a}$ receptor antagonists and for use in combination with adenosine $A_{2a}$ receptor antagonists include typical and atypical antipsychotic agents. Typical antipsychotics include loxapine, haloperidol, chlorpromazine, prochlorperazine and thiothixene. Atypical antipsychotics include clozapine, olanzapine, loxapine, quetiapine, ziprasidone and risperidone.

Tricyclic antidepressants causing dystonia treated by adenosine $A_{2a}$ receptor antagonists include perphenazine, amitriptyline, desipramine, doxepin, trimipramine and protriptyline. Anticonvulsants which may cause dystonia, but which also may be useful in treating ERLS or PLMS include phenyloin, carbamazepine and gabapentin.

Dopamine agonists useful in treating RLS and PLMS include pergolide, pramipexole, ropinerole, fenoldopam and cabergoline.

Opioids useful in treating PRLS and PLMS include codeine, hydrocodone, oxycodone, propoxyphene and tramadol.

Benzodiazepines useful in treating PRLS and PLMS include clonazepam, triazolam and temazepam.

The antipsychotics, tricyclic antidepressants, anticonvulsants, dopamine agonists, opioids and benzodiazepines are commercially available and are described in the literature, e.g., in The Physicians' Desk Reference (Montvale: Medical Economics Co., Inc., 2001).

One to three other agents can be used in combination with the compounds of formula I, preferably one.

The pharmacological activity of the compounds of the invention was determined by the following in vitro and in vivo assays to measure $A_{2a}$ receptor activity.

Human Adenosine $A_{2a}$ and $A_1$ Receptor Competition Binding Assay Protocol

Membrane Sources:

$A_{2a}$: Human $A_{2a}$ Adenosine Receptor membranes, Catalog #RB-HA2a, Receptor Biology, Inc., Beltsville, Md. Dilute to 17 µg/100 µl in membrane dilution buffer (see below).

Assay Buffers:

Membrane dilution buffer: Dulbecco's Phosphate Buffered Saline (Gibco/BRL)+10 mM $MgCl_2$.

Compound Dilution Buffer: Dulbecco's Phosphate Buffered Saline (Gibco/BRL)+10 mM $MgCl_2$ supplemented with 1.6 mg/ml methyl cellulose and 16% DMSO. Prepared fresh daily.

Ligands:

$A_{2a}$: [3H]-SCH 58261, custom synthesis, AmershamPharmacia Biotech, Piscataway, N.J. Stock is prepared at 1 nM in membrane dilution buffer. Final assay concentration is 0.5 nM.

$A_1$: [3H]-DPCPX, AmershamPharmacia Biotech, Piscataway, N.J. Stock is prepared at 2 nM in membrane dilution buffer. Final assay concentration is 1 nM.

Non-Specific Binding:

$A_{2a}$: To determine non-specific binding, add 100 nM CGS 15923 (RBI, Natick, Mass.). Working stock is prepared at 400 nM in compound dilution buffer.

$A_1$: To determine non-specific binding, add 100 µM NECA (RBI, Natick, Mass.). Working stock is prepared at 400 µM in compound dilution buffer.

Compound Dilution:

Prepare 1 mM stock solutions of compounds in 100% DMSO. Dilute in compound dilution buffer. Test at 10 concentrations ranging from 3 µM to 30 pM. Prepare working solutions at 4× final concentration in compound dilution buffer.

Assay Procedure:

Perform assays in deep well 96 well plates. Total assay volume is 200 µl. Add 50 µl compound dilution buffer (total ligand binding) or 50 µl CGS 15923 working solution ($A_{2a}$ non-specific binding) or 50 µl NECA working solution ($A_1$ non-specific binding) or 50 µl of drug working solution. Add 50 µl ligand stock ([3H]-SCH 58261 for $A_{2a}$, [3H]-DPCPX for $A_1$). Add 100 µl of diluted membranes containing the appropriate receptor. Mix. Incubate at room temperature for 90 minutes. Harvest using a Brandel cell harvester onto Packard GF/B filter plates. Add 45 µl Microscint 20 (Packard), and count using the Packard TopCount Microscintillation Counter. Determine $IC_{50}$ values by fitting the displacement curves using an iterative curve fitting program (Excel). Determine Ki values using the Cheng-Prusoff equation.

Haloperidol-Induced Catalepsy in the Rat

Male Sprague-Dawley rats (Charles River, Calco, Italy) weighing 175-200 g are used. The cataleptic state is induced by the subcutaneous administration of the dopamine receptor antagonist haloperidol (1 mg/kg, sc), 90 min before testing the animals on the vertical grid test. For this test, the rats are placed on the wire mesh cover of a 25×43 plexiglass cage placed at an angle of about 70 degrees with the bench table. The rat is placed on the grid with all four legs abducted and extended ("frog posture"). The use of such an unnatural posture is essential for the specificity of this test for catalepsy. The time span from placement of the paws until the first complete removal of one paw (decent latency) is measured maximally for 120 sec.

The selective $A_{2A}$ adenosine antagonists under evaluation are administered orally at doses ranging between 1 and 30 mg/kg, 1 and 4 h before scoring the animals. Also, the selective $A_{2A}$ adenosine antagonists under evaluation are administered subcutaneously at doses ranging between 10 and 30 mg/kg, 1 and 4 h before scoring the animals.

6-OHDA Lesion of the Middle Forebrain Bundle in Rats

Adult male Sprague-Dowley rats (Charles River, Calco, Como, Italy), weighing 275-300 g, are used in all experiments. The rats are housed in groups of 4 per cage, with free access to food and water, under controlled temperature and 12 hour light/dark cycle. The day before the surgery the rats are fasted over night with water ad libitum.

Unilateral 6-hydroxydopamine (6-OHDA) lesion of the middle forebrain bundle is performed according to the method described in Ungerstedt et al, *Brian Research*, 24 (1970), p. 485-493, and Ungerstedt, *Eur. J. Pharmacol.*, 5 (1968), p. 107-110, with minor changes. Briefly, the animals are anaesthetized with chloral hydrate (400 mg/kg, ip) and treated with desipramine (10 mpk, ip) 30 min prior to 6-OHDA injection in order to block the uptake of the toxin by the noradrenergic terminals. Then, the animals are placed in a stereotaxic frame. The skin over the skull is reflected and the stereotaxic coordinates (−2.2 posterior from bregma (AP), +1.5 lateral from bregma (ML), 7.8 ventral from dura (DV) are taken, according to the atlas of Pellegrino et al (Pellegrino L. J., Pellegrino A. S. and Cushman A. J., *A Stereotaxic Atlas of the Rat Brain*, 1979, New York: Plenum Press). A burr hole is then placed in the skull over the lesion site and a needle, attached to a Hamilton syringe, is lowered into the left MFB. Then 8 µg 6-OHDA-HCl is dissolved in 4 µl of saline with 0.05% ascorbic acid as antioxidant, and infused at the constant flow rate of 1 µl/1 min using an infusion pump. The needle is withdrawn after additional 5 min and the surgical wound is closed and the animals left to recover for 2 weeks.

Two weeks after the lesion the rats are administered with L-DOPA (50 mg/kg, ip) plus Benserazide (25 mg/kg, ip) and selected on the basis of the number of full contralateral turns quantified in the 2 h testing period by automated rotameters (priming test). Any rat not showing at least 200 complete turns/2 h is not included in the study.

Selected rats receive the test drug 3 days after the priming test (maximal dopamine receptor supersensitivity). The new $A_{2A}$ receptor antagonists are administered orally at dose levels ranging between 0.1 and 3 mg/kg at different time points (i.e., 1, 6, 12 h) before the injection of a subthreshold dose of L-DOPA (4 mpk, ip) plus benserazide (4 mpk, ip) and the evaluation of turning behavior.

Using the above test procedures, the following results were obtained for preferred and/or representative compounds of the invention.

Results of the binding assay on compounds of the invention showed $A_{2a}$ Ki values of about 4 to about 1800 nM, with preferred compounds showing Ki values between 4 and 100 nM, more preferably between 4 and 20 nM. Representative preferred compounds and their Ki values are listed in the following table:

| Example | Ki (nM) |
|---------|---------|
| 3 | 17.6 |
| 8 | 12 |
| 12 | 12.2 |
| 13 | 4.7 |
| 31 | 6.2 |

Selectivity is determined by dividing Ki for A1 receptor by Ki for A2a receptor. Compounds of the invention have a selectivity ranging from about 1 to about 1600. Preferred are compounds are those wherein the selectivity is >100.

Preferred compounds showed about a 20-40% decrease in descent latency when tested for anti-cataleptic activity in rats.

One to three compounds of formula I can be administered in the method of the invention, preferably one.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 70 percent active ingredient. Suitable solid carriers are known in the art, e.g. magnesium carbonate, magnesium stearate, talc, sugar, lactose. Tablets, powders, cachets and capsules can be used as solid dosage forms suitable for oral administration.

For preparing suppositories, a low melting wax such as a mixture of fatty acid glycerides or cocoa buffer is first melted, and the active ingredient is dispersed homogeneously therein as by stirring. The molten homogeneous mixture is then poured into convenient sized molds, allowed to cool and thereby solidify.

Liquid form preparations include solutions, suspensions and emulsions. As an example may be mentioned water or water-propylene glycol solutions for parenteral injection.

Liquid form preparations may also include solutions for intranasal administration.

Aerosol preparations suitable for inhalation may include solutions and solids in powder form, which may be in combination with a pharmaceutically acceptable carrier, such as an inert compressed gas.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in unit dosage form. In such form, the preparation is subdivided into unit doses containing appropriate quantities of the active component, e.g., an effective amount to achieve the desired purpose.

The quantity of active compound of formula I in a unit dose of preparation may be varied or adjusted from about 0.1 mg to 1000 mg, more preferably from about 1 mg to 300 mg, according to the particular application.

The actual dosage employed may be varied depending upon the requirements of the patient and the severity of the condition being treated. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The amount and frequency of administration of the compounds of the invention and the pharmaceutically acceptable salts thereof will be regulated according to the judgment of the attending clinician considering such factors as age, condition and size of the patient as well as severity of the symptoms being treated. A typical recommended dosage regimen for compounds of formula I is oral administration of from 10 mg to 2000 mg/day preferably 10 to 1000 mg/day, in two to four divided doses to provide relief from central nervous system diseases such as Parkinson's disease or the other disease or conditions listed above.

The doses and dosage regimen of the other agents used in the treatment of Parkinson's disease will be determined by the attending clinician in view of the approved doses and dosage regimen in the package insert, taking into consideration the age, sex and condition of the patient and the severity of the disease. It is expected that when the combination of a compound of formula I and another agent useful for treating Parkinson's disease, EPS, dystonia, RLS or PLMS is administered, lower doses of the components will be effective compared to the doses of the components administered as monotherapy. When administered in combination, the compound(s) of formula I and the other agent(s) for treating Parkinson's disease, EPS, dystonia, RLS or PLMS can be administered simultaneously or sequentially. This is particularly useful when the components of the combination are preferably given on different dosing schedules, e.g., one component is administered daily and another every six hours, or when the preferred pharmaceutical compositions are different, e.g. one is preferably a tablet and one is a capsule. A kit comprising the separate dosage forms is therefore advantageous.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

We claim:
1. A compound represented by the structural formula

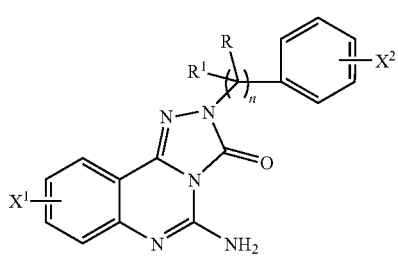

or a pharmaceutically acceptable salt thereof, wherein:
- $X^1$ is 1-3 substituents independently selected from the group consisting of H, alkyl, halo, —$CF_3$, —$OCF_3$, alkoxy, —OH and —CN;
- $X^2$ is 1-3 substituents independently selected from the group consisting of H, alkyl, halo, —$CF_3$, —$OCF_3$, alkoxy, —OH and —CN;
- n is 0, 1 or 2; and
- R and $R^1$ are independently selected from the group consisting of H and alkyl.

2. A compound of claim 1 wherein n is 1.
3. A compound of claim 1 wherein R and $R^1$ are each H.
4. A compound of claim 1 wherein $X^1$ is 1 or 2 substituents independently selected from H, halo, alkyl, alkoxy and —$CF_3$.
5. A compound of claim 4 wherein $X^1$ is 1 or 2 substituents independently selected from H, fluoro, chloro, methyl, methoxy and —$CF_3$.
6. A compound of claim 1 wherein $X^2$ is 1, 2 or 3 substituents independently selected from H, halo, alkyl, alkoxy, —$CF_3$, —$OCF_3$ and —CN.
7. A compound of claim 6 wherein $X^2$ is 1, 2 or 3 substituents independently selected from H, fluoro, chloro, methyl, methoxy, —$CF_3$, —$OCF_3$ and —CN.
8. A compound of claim 1 wherein n is 1; R and $R^1$ are each H; $X^1$ is 1 or 2 substituents independently selected from H, halo, alkyl, alkoxy and —$CF_3$; and $X^2$ is 1, 2 or 3 substituents independently selected from H, halo, alkyl, alkoxy, —$CF_3$, —$OCF_3$ and —CN.
9. A compound of claim 8 wherein $X^1$ is 1 or 2 substituents independently selected from H, fluoro, chloro, methyl, methoxy and —$CF_3$, and $X^2$ is 1, 2 or 3 substituents independently selected from H, fluoro, chloro, methyl, methoxy, —$CF_3$, —$OCF_3$ and —CN.
10. A compound of claim 1 selected from the group consisting of

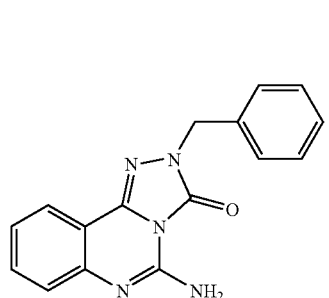 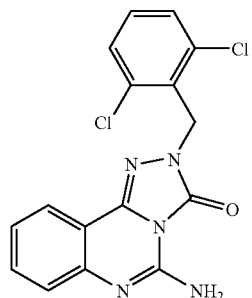

-continued

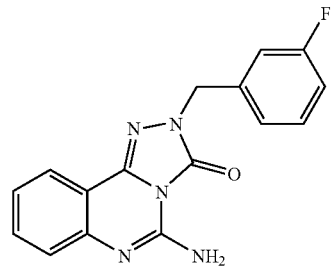

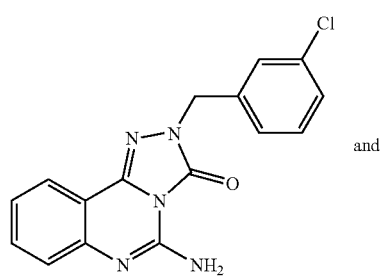 and

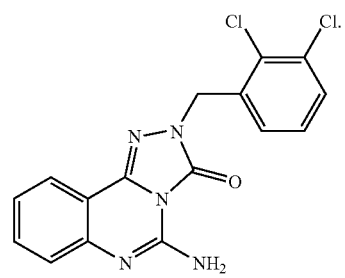

11. A pharmaceutical composition comprising a therapeutically effective amount of a compound of claim 1 in a pharmaceutically acceptable carrier.

12. A pharmaceutical composition comprising a therapeutically effective amount of a combination of a compound of claim 1 and one to three other agents useful in treating Parkinson's disease in a pharmaceutically acceptable carrier.

13. A kit comprising in separate containers in a single package pharmaceutical compositions for use in combination to treat Parkinson's disease wherein one container comprises a pharmaceutical composition comprising an effective amount of a compound of claim 1 in a pharmaceutically acceptable carrier, and wherein, in separate containers, one or more pharmaceutical compositions each comprise an effective amount of an agent useful in the treatment of Parkinson's disease in a pharmaceutically acceptable carrier.

* * * * *